(12) United States Patent
Sullivan

(10) Patent No.: US 7,654,962 B2
(45) Date of Patent: Feb. 2, 2010

(54) RADIATION STRESS NON-INVASIVE BLOOD PRESSURE METHOD

(75) Inventor: Patrick K. Sullivan, Kailua, HI (US)

(73) Assignee: Hoana Medical, Inc., Honolulu, HI (US)

( * ) Notice: Subject to any disclaimer, the term of this patent is extended or adjusted under 35 U.S.C. 154(b) by 330 days.

(21) Appl. No.: 10/562,416

(22) PCT Filed: Jun. 28, 2004

(86) PCT No.: PCT/US2004/020767

§ 371 (c)(1),
(2), (4) Date: Dec. 23, 2005

(87) PCT Pub. No.: WO2005/000108

PCT Pub. Date: Jan. 6, 2005

(65) Prior Publication Data

US 2007/0265535 A1    Nov. 15, 2007

Related U.S. Application Data

(60) Provisional application No. 60/482,460, filed on Jun. 26, 2003.

(51) Int. Cl.
*A61B 5/02* (2006.01)
*A61B 5/00* (2006.01)

(52) U.S. Cl. .................. 600/481; 600/483; 600/485; 600/300

(58) Field of Classification Search .............. 600/300, 600/481, 483, 484, 485, 488, 500–503, 508–526
See application file for complete search history.

(56) References Cited

U.S. PATENT DOCUMENTS

| | | | |
|---|---|---|---|
| 4,245,648 A | 1/1981 | Trimmer et al. | |
| 4,320,766 A | 3/1982 | Alihanka et al. | |
| 4,429,699 A | 2/1984 | Hatschek | |
| 4,459,991 A | 7/1984 | Hatschek | |
| 4,475,557 A | 10/1984 | Hatschek et al. | |
| 4,509,527 A | 4/1985 | Fraden | |
| 4,562,723 A | 1/1986 | Hubner | |
| 4,695,955 A | 9/1987 | Faisandier | |
| 4,827,763 A | 5/1989 | Bourland et al. | |
| 4,926,866 A | 5/1990 | Lee | |
| 4,961,428 A * | 10/1990 | Nikias et al. | ................ 600/512 |

(Continued)

FOREIGN PATENT DOCUMENTS

WO    WO 03/082111    10/2003

OTHER PUBLICATIONS

International Search Report for PCT Application No. PCT/US2004/020767.

*Primary Examiner*—Charles A Marmor, II
*Assistant Examiner*—Navin Natnithithadha
(74) *Attorney, Agent, or Firm*—Fulwider Patton LLP

(57) ABSTRACT

The invention determines the energy dispersion via acoustic, electromechanical or other related physiological signals collected from a patient that lies down or otherwise engages a discritized sensing array. Signals are monitored over a range of frequencies and collected in the time domain or frequency domain. A computing machine determines the energy from the signal measured over various elements of the array and calculates the momentum flux. Blood pressure is determined directly from the momentum flux calculation.

26 Claims, 3 Drawing Sheets

U.S. PATENT DOCUMENTS

| | | | |
|---|---|---|---|
| 4,974,598 A * | 12/1990 | John | 600/509 |
| 5,002,060 A | 3/1991 | Nedivi | |
| 5,137,033 A | 8/1992 | Norton | |
| 5,144,284 A | 9/1992 | Hammett | |
| 5,241,964 A | 9/1993 | McQuilkin | |
| 5,282,474 A | 2/1994 | Valdes Sosa et al. | |
| 5,292,340 A | 3/1994 | Crosby et al. | |
| 5,309,916 A | 5/1994 | Hatschek | |
| 5,448,996 A | 9/1995 | Belin et al. | |
| 5,515,865 A | 5/1996 | Scanlon | |
| 5,590,650 A | 1/1997 | Genova | |
| 5,808,552 A | 9/1998 | Wiley et al. | |
| 5,846,206 A | 12/1998 | Bader | |
| 5,853,005 A | 12/1998 | Scanlon | |
| 5,942,979 A | 8/1999 | Luppino | |
| 5,964,720 A | 10/1999 | Pelz | |
| 5,989,193 A | 11/1999 | Sullivan | |
| 6,014,346 A | 1/2000 | Malone | |
| 6,047,203 A | 4/2000 | Sackner et al. | |
| 6,050,940 A | 4/2000 | Braun et al. | |
| 6,146,332 A | 11/2000 | Pinsonneault et al. | |
| 6,195,008 B1 | 2/2001 | Bader | |
| 6,198,394 B1 | 3/2001 | Jacobsen et al. | |
| 6,248,064 B1 | 6/2001 | Gopinathan et al. | |
| 6,261,237 B1 | 7/2001 | Swanson et al. | |
| 6,280,392 B1 | 8/2001 | Yoshimi et al. | |
| 6,315,719 B1 | 11/2001 | Rode et al. | |
| 6,375,621 B1 | 4/2002 | Sullivan | |
| 6,402,691 B1 | 6/2002 | Peddicord et al. | |
| 6,445,299 B1 | 9/2002 | Rojas, Jr. | |
| 6,450,957 B1 | 9/2002 | Yoshimi et al. | |
| 6,468,234 B1 * | 10/2002 | Van der Loos et al. | 600/595 |
| 6,475,153 B1 | 11/2002 | Khair et al. | |
| 6,497,658 B2 | 12/2002 | Roizen et al. | |
| 6,506,153 B1 | 1/2003 | Littek et al. | |
| 6,540,673 B2 | 4/2003 | Gopinathan et al. | |
| 6,547,743 B2 | 4/2003 | Brydon | |
| 6,575,902 B1 | 6/2003 | Burton | |
| 6,648,828 B2 | 11/2003 | Friedman et al. | |
| 6,652,466 B2 | 11/2003 | Sugo et al. | |
| 6,689,069 B2 | 2/2004 | Bratteli et al. | |
| 6,746,403 B2 | 6/2004 | Kolluri et al. | |
| 6,826,426 B2 | 11/2004 | Lange et al. | |
| 6,984,207 B1 | 1/2006 | Sullivan et al. | |
| 6,988,989 B2 | 1/2006 | Weiner et al. | |
| 7,314,451 B2 * | 1/2008 | Halperin et al. | 600/534 |
| 2003/0018241 A1 | 1/2003 | Mannheimer | |
| 2004/0111045 A1 | 6/2004 | Sullivan et al. | |
| 2005/0190062 A1 | 9/2005 | Sullivan et al. | |
| 2005/0190068 A1 | 9/2005 | Gentry et al. | |
| 2006/0063982 A1 | 3/2006 | Sullivan et al. | |

* cited by examiner

RADIATION STRESS NON-INVASIVE BLOOD PRESSURE METHOD

RELATED APPLICATIONS

This application is the National Stage of International Application No. PCT/US2004/020767, filed Jun. 28, 2004, which claims the benefit of U.S. Provisional Application No. 60/482,460, filed Jun. 26, 2003.

BACKGROUND OF THE INVENTION

Current methods for measurement of blood pressure and other vital signs are inefficient. Many measurements of patient vital signs are invasive procedures that are uncomfortable or inconvenient for the patient. Typically, the measurement of blood pressure requires the use of a cuff around the arm of a patient and is a non-continuous "spot-check" that does not reflect the true state of patient physiology.

Needs exist for improved methods of continuous non-invasive blood pressure measurements.

SUMMARY OF THE INVENTION

The present invention is a system that provides non-invasive, real-time, continuous collection and processing of signals from a patient to determine the current condition of the patient. The present invention relates preferably to the measurement of blood pressure. This measurement includes the average, mean, systolic and diastolic arterial blood pressure. However, the present invention is not limited to the measurement of blood pressure; other vital signs can be measured and processed as well. The present method also provides for continuous, non-invasive monitoring of hypertension and other related medical conditions.

The present invention uses acoustic, electromechanical or other related physiological signals collected from a patient. To operate the monitoring device, the patient engages discritized, discrete, separated sensors in one or more discrete sensing arrays installed in a bed, chair or any other equipment that the patient will use. The patient lies down on, sits on, stands on, or otherwise engages the discritized sensing array, and signals are monitored over a range of frequencies or at a specific frequency. Data is collected as a time series or another similar method. Data is transferred to a computing device in the form of a voltage signal via wire, fiber optics or wireless technology.

The energy spectra of each array point are determined and then are used to determine the variance of each array. Computational analysis of the data collected is used to determine energy momentum flux of blood flowing through the patient. Non-time series methods are used to determine energy at various array points or at a combination of array points. Momentum flux is determined from the data collected by the discritized separate sensors in each array. Blood pressure is related to the momentum flux through a mathematical algorithm. A computing device performs the computation of blood pressure.

These and further and other objects and features of the invention are apparent in the disclosure, which includes the above and ongoing written specification, with the claims and the drawings.

DETAILED DESCRIPTION OF THE PREFERRED EMBODIMENTS

The present invention is a system that provides real-time, continuous collection and processing of signals from a patient to determine the condition of the patient. The present invention relates preferably to the measurement of blood pressure. The measurements include the average, mean, systolic and diastolic arterial blood pressure. The present invention is not limited to the measurement of blood pressure; other vital functions, for example, heart rate and pulses and electrical signals, can be measured and processed as well. The present method provides for continuous, non-invasive monitoring of hypertension and other related medical conditions.

Figures 1, 2:
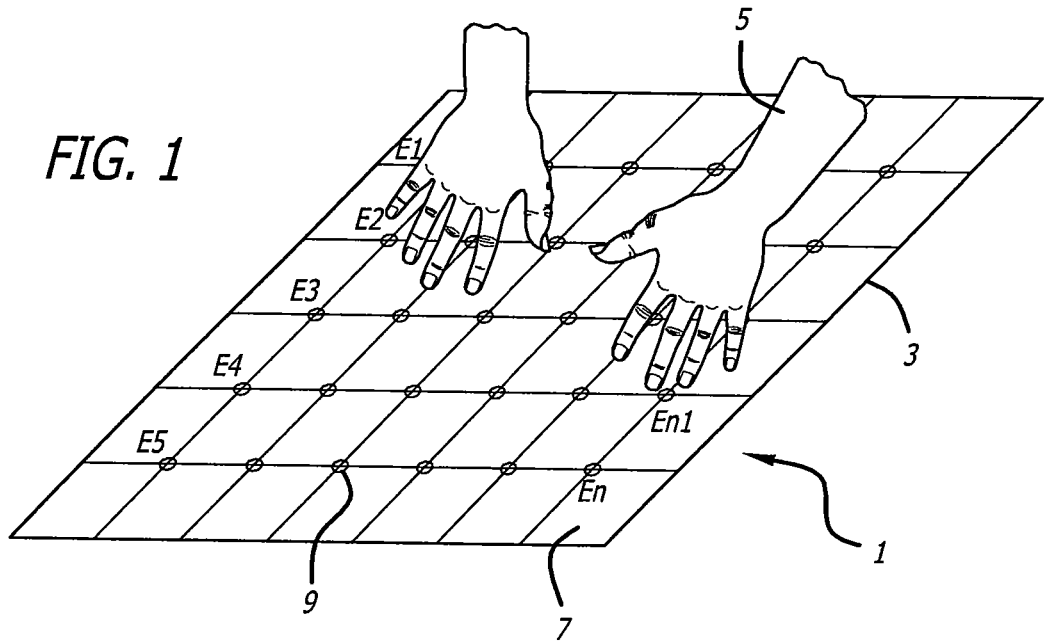
FIG. 1 is a diagram of the monitoring system with a discritized array.
FIG. 2 is a diagram of energy spectra collected from location 1 to location n.
Figure 3:
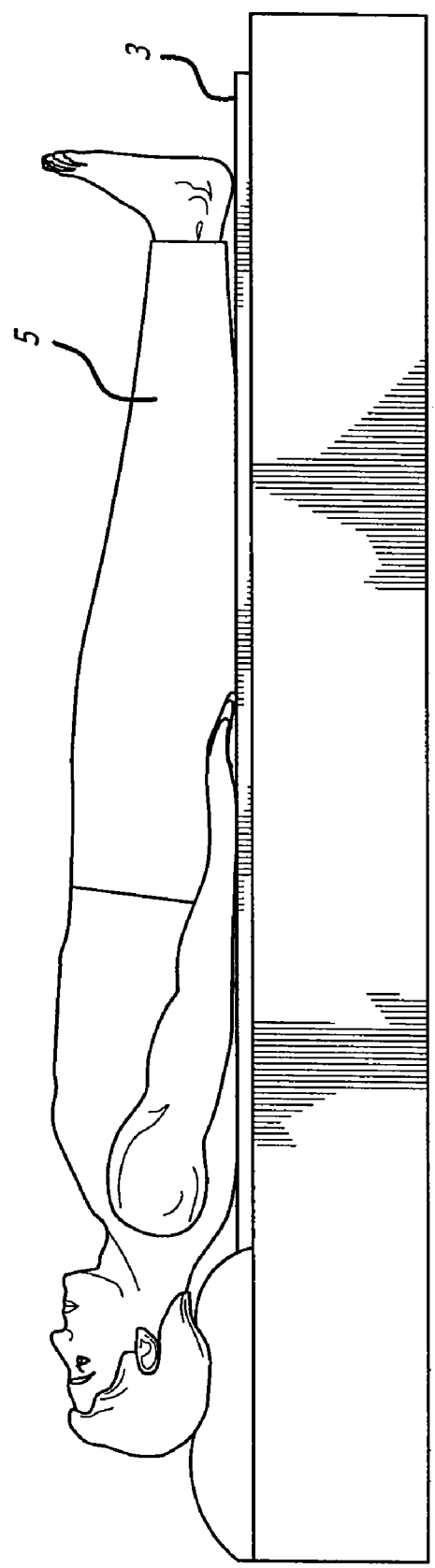
FIG. 3 is a schematic representation of a person lying on an array of sensors.

FIG. 1 shows a diagram of a monitoring system 1 and a discritized array 3 of separate sensors 9. The present invention uses acoustic, electromechanical or other related physiological signals collected from a patient 5 in contact with the discritized sensors in the sensing array 3. The discritized sensing array 3 is a relatively flat device 7 with individual sensing arrays 9 dispersed throughout the surface of the discritized sensing array 3. The patient 5 lies down on, stands on, or otherwise engages the discritized sensing array 3, and signals are monitored over a range of frequencies or at a specific frequency, as shown in FIG. 3. Data is collected as a time series or another similar method. Data is collected from individual sensing arrays 9, from grid locations 1 to n, via acoustic, electromechanical or other physiological signals.

Figure 4:
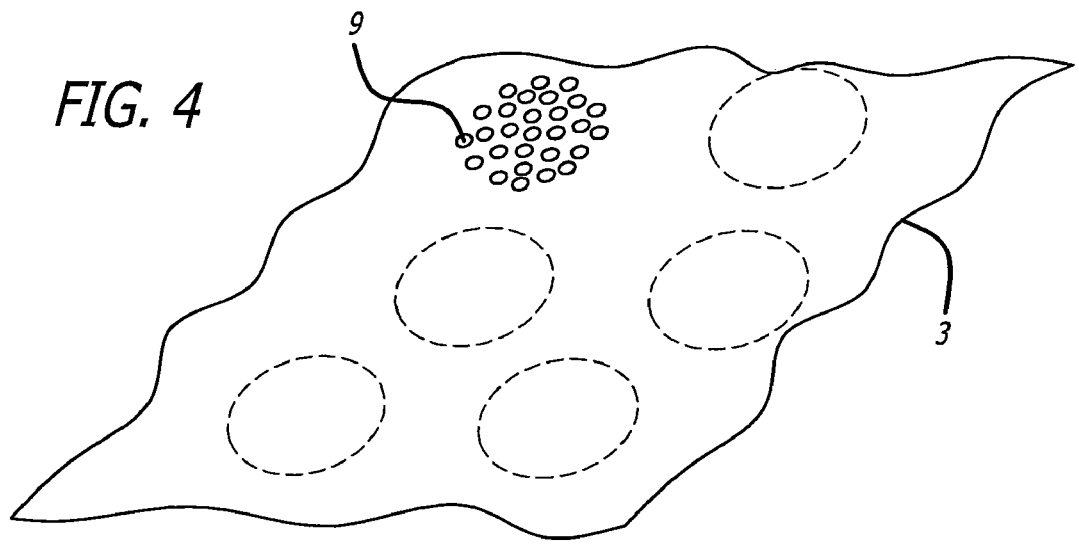
FIGS. 4 and 5 are schematic representations of portions of sheets with sensor arrays.
Figure 5:
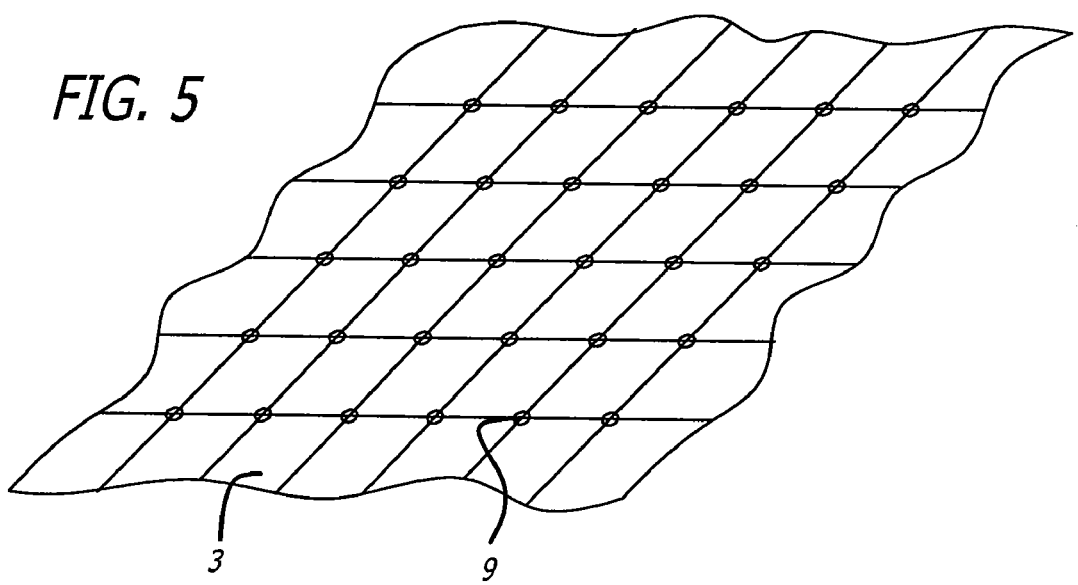

The discritized sensing array 3 can have sensors arranged in various regular or irregular configurations. FIG. 4 and FIG. 5 show different arrangements of individual sensors 9 on a portion of the large discritized sensing array.

The discritized sensing array 3 provides time series data that is analyzed to produce energy spectra at locations 1 to n, as shown in FIG. 2. The data is used to determine the variance of the time series signals. Computational analysis of data collected is used to determine momentum flux of energy through the patient.

Blood pressure is related to the momentum flux through a mathematical model. The following relationship relates the incoming data to blood pressure:

$Pa = K^*(E1-En)$ = Average pressure due to excess flow of momentum

Pa = Average blood pressure

K = Constant

E1 = Summation of energy spectra (area under the curve—variance of time series) at location 1×Pulse wave velocity En = Summation of energy spectra (area under the curve—variance of time series) at location n×Pulse wave velocity A computing device performs the computation of blood pressure. The results of computation are output to the user.

The radiation stress, non-invasive blood pressure device of the present invention uses time series analysis and computational methods to process acoustic, electromechanical or other physiological signals from the patient. An energy spectrum is created by the sensing arrays to calculate the variance.

The variance is the area under the energy spectra curve. Non-time series methods are used to determine energy at various array points.

While the invention has been described with reference to specific embodiments, modifications and variations of the invention may be constructed without departing from the scope of the invention, which is described in the following claims.

The invention claimed is:

1. A radiation stress, non-invasive vital sign monitoring method comprising:
   providing one or more discretized sensor arrays,
   engaging the one or more discretized sensor arrays,
   measuring and collecting discretized acoustic or electromechanical or physiological signals with the discretized sensor arrays,
   transmitting discretized signals to a receiving and computer device,
   the receiving and computer device
   produces time series data from various discretized sensor array signals,
   calculates energy spectrum from the time series data,
   determines variance of each discretized sensor array, and
   calculates a value for vital signs of a patient.

2. The method of claim 1, wherein the vital signs are average, mean, systolic and diastolic arterial blood pressure.

3. The method of claim 1, wherein the vital signs are hypertension.

4. The method of claim 1, further comprising lying on, standing on, or otherwise contacting the discretized sensor arrays.

5. The method of claim 1, wherein the collecting the discretized acoustic or electromechanical physiological signals is performed over a range of frequencies.

6. The method of claim 1, wherein the collecting the discretized acoustic or electromechanical physiological signals is performed over a single frequency.

7. The method of claim 1, wherein the collecting acoustic or electromechanical physiological signals further comprises collecting data in a time domain or frequency domain.

8. The method of claim 1, wherein the calculating a value for vital signs is performed with non-time series methods for determining energy at various array points or a combination of array points.

9. The method of claim 1, wherein the transmitting of discretized signals comprises transmitting discretized signals via wire, fiber optics or wirelessly.

10. The method of claim 1, further comprising providing continuous, real-time monitoring of a patient's vital signs.

11. The method of claim 1, further comprising calculating the momentum flux from data gathered from the discretized sensor arrays.

12. The method of claim 11, further comprising calculating a patient's vital signs from the momentum flux.

13. The method of claim 1, wherein the one or more discretized sensor arrays are not attached to the patient.

14. A radiation stress, non-invasive vital sign monitoring device comprising:
    one or more discretized sensor arrays for measuring and collecting discretized acoustic or electromechanical signals from a patient,
    a surface on the one or more discretized sensor arrays for engaging a patient,
    a transmission system for transmitting data collected by the one or more discretized sensor arrays,
    a receiving device for receiving the transmitted data from the one or more discretized sensor arrays, and
    a computing device connected to the receiving device for calculating values of vital signs of the patient by
    producing time series data from various discretized sensor array signals,
    calculating energy spectrum from the time series data, and
    determining variance of each discretized sensor array.

15. The device of claim 14, wherein the vital signs are average, mean, systolic and diastolic arterial blood pressure.

16. The device of claim 14, wherein the vital signs are hypertension.

17. The device of claim 14, wherein the patient lies on, stands on, or otherwise contacts the discretized sensor arrays.

18. The device of claim 14, wherein the discretized sensor arrays collect the discretized acoustic or electromechanical signals over a range of frequencies.

19. The device of claim 14, wherein the discretized sensor arrays collect the discretized acoustic or electromechanical signals over a single frequency.

20. The device of claim 14, wherein the discretized sensor arrays collect the discretized acoustic or electromechanical signals in a time domain or frequency domain.

21. The device of claim 14, wherein the computing device calculates a value for vital signs with non-time series methods for determining energy at various array points or a combination of array points.

22. The device of claim 14, wherein the transmission system transmits discretized signals via wire, fiber optics or wirelessly.

23. The device of claim 14, wherein the discretized sensor arrays provide continuous, real-time monitoring of a patient's vital signs.

24. The device of claim 14, wherein the computing device computes the momentum flux from data gathered from the discretized sensor arrays.

25. The device of claim 24, wherein the computing device further computes a patient's vital signs from the momentum flux.

26. The device of claim 14, wherein the one or more discretized sensor arrays are not attached to the patient.

* * * * *

UNITED STATES PATENT AND TRADEMARK OFFICE
CERTIFICATE OF CORRECTION

PATENT NO. : 7,654,962 B2  Page 1 of 1
APPLICATION NO. : 10/562416
DATED : February 2, 2010
INVENTOR(S) : Patrick K. Sullivan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 736 days.

Signed and Sealed this

Twenty-eighth Day of December, 2010

David J. Kappos
*Director of the United States Patent and Trademark Office*